US012733821B2

(12) United States Patent
Yeo et al.

(10) Patent No.: US 12,733,821 B2
(45) Date of Patent: Sep. 15, 2026

(54) IMPLANTABLE CEREBRAL SENSING DEVICES AND SYSTEMS AND METHODS RELATED THERETO

(71) Applicant: Georgia Tech Research Corporation, Atlanta, GA (US)

(72) Inventors: Woon-Hong Yeo, Atlanta, GA (US); Robert Herbert, Atlanta, GA (US)

(73) Assignee: GEORGIA TECH RESEARCH CORPORATION, Atlanta, GA (US)

(*) Notice: Subject to any disclaimer, the term of this patent is extended or adjusted under 35 U.S.C. 154(b) by 1081 days.

(21) Appl. No.: 17/600,775

(22) PCT Filed: Apr. 1, 2020

(86) PCT No.: PCT/US2020/026100
§ 371 (c)(1),
(2) Date: Oct. 1, 2021

(87) PCT Pub. No.: WO2020/205925
PCT Pub. Date: Oct. 8, 2020

(65) Prior Publication Data

US 2022/0192518 A1 Jun. 23, 2022

Related U.S. Application Data

(60) Provisional application No. 62/827,999, filed on Apr. 2, 2019.

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0031* (2013.01); *A61B 5/0285* (2013.01);
(Continued)

(58) Field of Classification Search
CPC .............. A61B 5/02007; A61B 5/0031; A61B 5/0285; A61B 5/293; A61B 5/686;
(Continued)

(56) References Cited

U.S. PATENT DOCUMENTS 4,324,259 A 4/1982 Wrigth
2013/0041244 A1* 2/2013 Woias .................... G01L 1/142 600/381

(Continued)

FOREIGN PATENT DOCUMENTS

WO 2016/114468 A1 7/2016
WO WO-2017205718 A1 * 11/2017 ............ A61B 5/021
WO 2018/0220143 A1 12/2018

OTHER PUBLICATIONS

Shafqat, S., Hoefnagels, J., Savov, A., Joshi, S., Dekker, R., & Geers, M. (2017). Ultra-stretchable interconnects for high-density stretchable electronics. Micromachines, 8(9), 277. https://doi.org/10.3390/mi8090277 (Year: 2017).*

(Continued)

*Primary Examiner* — Jennifer Robertson
*Assistant Examiner* — Elina Sohyun Jang
(74) *Attorney, Agent, or Firm* — TROUTMAN PEPPER LOCKE LLP; Ryan A. Schneider; Nicholas H. Doss

(57) ABSTRACT

Disclosed herein is an implantable cerebral sensor, comprising: an insulator layer; a first electrode disposed on the first insulator: a dielectric layer disposed on the first electrode; and a second electrode disposed on the dielectric layer, the second electrode being electrically separated from the first electrode by the dielectric layer. The first electrode and the second electrode can comprise a conductor, and the insulator layer and the dielectric layer can comprise a polymer. The sensor can be configured to sense a condition in a blood vessel and generate a wireless signal indicative of the sensed (Continued)

condition. Also disclosed herein are systems using the disclosed implantable cerebral sensors and methods of making and using the same.

20 Claims, 13 Drawing Sheets

(51) Int. Cl.
*A61B 5/0285* (2006.01)
*A61B 5/293* (2021.01)
*H01B 1/02* (2006.01)
*H01B 3/30* (2006.01)

(52) U.S. Cl.
CPC .............. *A61B 5/293* (2021.01); *A61B 5/686* (2013.01); *H01B 1/02* (2013.01); *H01B 3/306* (2013.01); *A61B 2562/125* (2013.01); *A61B 2562/164* (2013.01)

(58) Field of Classification Search
CPC ........ A61B 2562/125; A61B 2562/164; A61B 5/02028; A61B 5/283; A61B 5/6868; H01B 1/02; H01B 3/306
See application file for complete search history.

(56) References Cited

U.S. PATENT DOCUMENTS

| | | | |
|---|---|---|---|
| 2014/0163390 | A1 | 6/2014 | Rogers et al. |
| 2015/0230742 | A1 | 8/2015 | Silver |
| 2015/0306282 | A1 | 10/2015 | Scanlon et al. |
| 2018/0199873 | A1 | 7/2018 | Wang et al. |

OTHER PUBLICATIONS

International Search Report and Written Opinion from PXT Application No. PCT/US2020/026100 dated Aug. 3, 2020.

Herbert, et al. "Fully Printed, Wireless, Stretchable Implantable Biosystem Toward Batteryless, Real-Time Monitoring of Cerebral Aneurysm Hemodynaics," Aug. 7, 2019; <https://onlinelibrary.wiley.com/doi/10.1002/advs.201901034>.

* cited by examiner

IMPLANTABLE CEREBRAL SENSING DEVICES AND SYSTEMS AND METHODS RELATED THERETO

CROSS-REFERENCE TO RELATED APPLICATIONS

This application claims the benefit of U.S. Provisional Application Ser. No. 62/827,999, filed on 2 Apr. 2019, the entire contents and substance of which is incorporated herein by reference in its entirety as if fully set forth below.

FIELD OF THE DISCLOSURE

The present disclosure relates generally to implantable cerebral sensing devices and systems. Particularly, embodiments of the present disclosure relate wireless implantable cerebral sensing devices and systems.

BACKGROUND

Cerebral aneurysms result from weakened sections of blood vessels allowing abnormal blood flow into a sac. The aneurysmal sac is the localized enlargement of the weakened vessel wall and can take on many forms, depending on geometry and location. There are many attributes such as vortices, velocities, and impinging regions within the sac. About 6% of the population is reported to experienced unruptured cerebral aneurysms. However, continuous incoming flow to the ballooned section of the vessel may cause rupture, often resulting in death or permanent damage. One of the most challenging locations for a cerebral aneurysm is in the highly contoured and narrow cerebral arteries. With these risks, it is critical to employ effective treatments and follow-up monitoring. Typical treatment methods seek to divert, impede, or reduce blood flow for preventing insertion to the aneurysmal sac. However, direct implantation of such devices does not provide monitoring capability, and therefore are not enough to conclude successful treatment. In the vascular system, implantable sensors must achieve high flexibilities while maintaining an extremely low-profile form in order to not disrupt or impede blood flow, particularly in cerebral arteries where vessel diameters are as low as 3 mm in diameter.

What is needed, therefore, is an implantable sensor for cerebral aneurysms that can monitor the internal conditions in cerebral blood vessels. Embodiments of the present disclosure address this need as well as other needs that will become apparent upon reading the description below in conjunction with the drawings.

BRIEF SUMMARY OF THE INVENTION

The present disclosure relates generally to implantable cerebral sensing devices and systems. Particularly, embodiments of the present disclosure relate wireless implantable cerebral sensing devices and systems. An exemplary embodiment of the present disclosure can provide an implantable cerebral sensor, comprising: an insulator layer; a first electrode disposed on the first insulator: a dielectric layer disposed on the first electrode; and a second electrode disposed on the dielectric layer, the second electrode being electrically separated from the first electrode by the dielectric layer. The first electrode and the second electrode can comprise a conductor, and the insulator layer and the dielectric layer can comprise a polymer. The sensor can be configured to sense a condition in a blood vessel and generate a wireless signal indicative of the sensed condition.

In any of the embodiments disclosed herein, the sensed condition in the blood vessel can be a hemodynamic property.

In any of the embodiments disclosed herein, the first electrode and the second electrode can have a thickness from 1 μm to 10 μm.

In any of the embodiments disclosed herein, the dielectric layer can have a thickness from 1 μm to 10 μm.

In any of the embodiments disclosed herein, the polymer can comprise a polyimide.

In any of the embodiments disclosed herein, the conductor can comprise metal nanoparticles.

In any of the embodiments disclosed herein, the implantable cerebral sensor can further comprise an outer shell substantially encasing the insulator layer, the first electrode, the dielectric layer, and the second electrode, the outer shell comprising an elastomer.

In any of the embodiments disclosed herein, the insulator layer and the dielectric layer can have a Young's modulus from 1 MPa to 100 GPa.

In any of the embodiments disclosed herein, the first electrode and the second electrode can have a Young's modulus from 1 GPa to 100 GPa.

In any of the embodiments disclosed herein, the implantable cerebral sensor can be deformably elastic when stretched from 250% to 1000% of the original length of the implantable cerebral sensor.

In any of the embodiments disclosed herein, the implantable cerebral sensor can have a capacitance from 50 pF to 100 pF between the first electrode and the second electrode.

In any of the embodiments disclosed herein, the implantable cerebral sensor can be a passive sensor.

Another embodiment of the present disclosure can provide a method of making an implantable cerebral sensor, the method comprising: atomizing a first ink comprising a polymer precursor and a first solvent; depositing the first ink onto a glass substrate to form a first insulator layer; treating the first insulator layer to cure the first insulator layer and to improve the surface adhesion of the first insulator layer; atomizing a second ink comprising conductive nanoparticles and a second solvent; depositing the second ink onto the first insulator layer to form a first electrode; depositing the first ink onto the first electrode to form a dielectric layer such that the first electrode is substantially encased by the dielectric layer; treating the dielectric layer to cure the dielectric layer and to improve the surface adhesion of the dielectric layer; and depositing the second ink onto the dielectric layer to form a second electrode.

In any of the embodiments disclosed herein, the method can further comprise encasing the implantable cerebral sensor in an elastomer layer.

In any of the embodiments disclosed herein, each of the depositing the second ink can further comprise sintering the first electrode and the second electrode.

In any of the embodiments disclosed herein, the depositing the second ink can form the first electrode and the second electrode to have a thickness from 1 μm to 10 μm.

In any of the embodiments disclosed herein, the depositing the first ink can form the dielectric layer to have a thickness from 1 μm to 10 μm.

In any of the embodiments disclosed herein, the polymer precursor can comprise a polyimide.

In any of the embodiments disclosed herein, the insulator layer and the dielectric layer can have a Young's modulus from 1 MPa to 100 GPa.

In any of the embodiments disclosed herein, the first electrode and the second electrode can have a Young's modulus from 1 GPa to 100 GPa.

In any of the embodiments disclosed herein, the implantable cerebral sensor can be deformably elastic when stretched from 250% to 1000% of the original length of the implantable cerebral sensor.

In any of the embodiments disclosed herein, the implantable cerebral sensor can have a capacitance from 50 pF to 100 pF between the first electrode and the second electrode.

In any of the embodiments disclosed herein, the method can further comprise integrating the implantable cerebral sensor in a stent configured to be implanted within a blood vessel.

In any of the embodiments disclosed herein, the ratio of the polymer precursor to the first solvent in the first ink can be 4:1 by volume.

Another embodiment of the present disclosure can provide a system for hemodynamic monitoring of blood vessels, the system comprising: an implantable cerebral sensor, comprising: an insulator layer comprising a polymer; a first electrode disposed on the first insulator, the first electrode comprising a conductor; a dielectric layer disposed on the first electrode, the dielectric layer comprising the polymer; and a second electrode disposed on the dielectric layer, the second electrode being electrically separated from the first electrode by the dielectric layer, the second electrode comprising the conductor; a function generator in electrical communication with an excitation coil; and an oscilloscope configured to receive a signal from an amplifier in electrical communication with a receiving coil, wherein a circuit is formed between the excitation coil, the implantable cerebral sensor, and the receiving coil.

In any of the embodiments disclosed herein, the system can be configured to: wirelessly transmit a first signal from the excitation coil to the implantable cerebral sensor; wirelessly receive a second signal at the receiving coil, the second signal being indicative of a change in the resonant frequency amplitude of the implantable cerebral sensor; and calculate a flow velocity of blood flowing through the implantable cerebral sensor based on the resonance frequency.

In any of the embodiments disclosed herein, the first electrode and the second electrode can have a thickness from 1 μm to 10 μm.

In any of the embodiments disclosed herein, the dielectric layer can have a thickness from 1 μm to 10 μm.

In any of the embodiments disclosed herein, the polymer can comprise a polyimide.

In any of the embodiments disclosed herein, the conductor can comprise metal nanoparticles.

In any of the embodiments disclosed herein, the implantable cerebral sensor can further comprise an outer shell substantially encasing the insulator layer, the first electrode, the dielectric layer, and the second electrode, the outer shell comprising an elastomer.

In any of the embodiments disclosed herein, the insulator layer and the dielectric layer can have a Young's modulus from 1 MPa to 100 GPa.

In any of the embodiments disclosed herein, the first electrode and the second electrode can have a Young's modulus from 1 GPa to 100 GPa.

In any of the embodiments disclosed herein, the implantable cerebral sensor can be deformably elastic when stretched from 250% to 1000% of the original length of the implantable cerebral sensor.

In any of the embodiments disclosed herein, the implantable cerebral sensor can have a capacitance from 50 pF to 100 pF between the first electrode and the second electrode.

In any of the embodiments disclosed herein, the implantable cerebral sensor can be integrated in a stent and implanted within a blood vessel.

These and other aspects of the present invention are described in the Detailed Description of the Invention below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION

Figure 1:
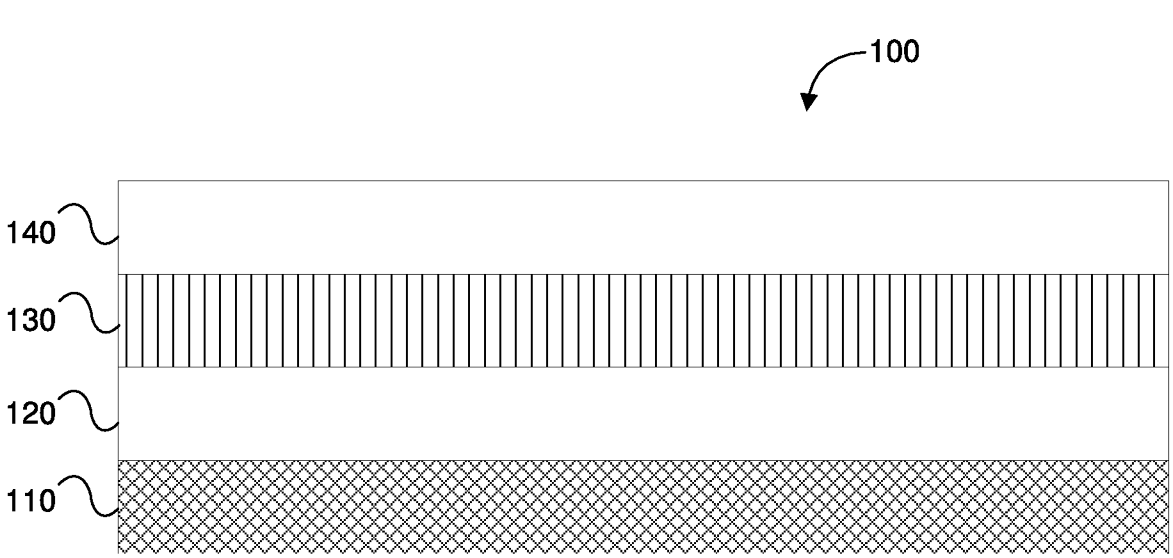
FIG. 1 illustrates a cross-sectional view of an implantable cerebral sensor according to some examples of the present disclosure.

Disclosed herein is a flow-sensing method utilizing a nanostructured capacitive sensor to quantify intra-aneurysmal blood flow. Recent advancements in soft electronics and sensors offer capabilities that were limited by rigid systems. Also disclosed herein is a soft, stretchable, flexible, low-profile sensor system to overcome the challenged of cerebral intravenous navigation and deployment. The low-profile, elastomer-encased design of the disclosed sensor can conform to a flow diverter, such as a stent, and normal blood flow path, maintaining the wall perforation risk mitigation desired with flow diversion. The highly compliant disclosed sensors can be integrated with a flow diverter and can be easily embedded in a catheter, enabling safe travel through the complex neurovascular anatomy to a targeted cerebral aneurysm.

To aid in the fabrication of the disclosed sensors, the disclosed methods of making the same utilize aerosol jet printing (AJP), which can address the issues of conventional fabrication techniques. AJP, compared to conventional processes, allows for faster and more reliable fabrication and scalable manufacturing via direct printing, digital designing, and optimized control. The disclosed methods can create a fully passive, wireless, low-profile capacitive sensor and coil inductor with enhanced readout distance via comprehensive understanding and optimization of AJP materials and fabrication methods. As used herein, the term "passive" means that the sensor does not require an external power source, e.g., a battery, for operation. Such fully additive processes can involve high-precision printing of aligned layers followed by seamless integration on a soft elastomer.

Therefore, the disclosed systems, devices, and methods can provide improved implantable cerebral sensors and monitoring of hemodynamics in blood vessels. The disclosed sensors can be extremely low-profile and have a stretchable structure to allow the device to be conformally integrated onto a medical stent and deployed via conventional catheter procedures. Utilization of a disclosed inductive coupling method to monitor hemodynamics can enable a battery-less, wireless detection of the disclosed sensors at distances surpassing existing devices.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter.

As used herein, the term "nanoparticle" refers to a particle having at least one dimension that is no greater than 500 nm. In some embodiments, "nanoparticles" can have at least one dimension that is no greater than 100 nm. The term "nanoparticle" can include, for example, "nanospheres," "nanorods," "nanocups," "nanowires," "nanoclusters," "nanolayers," "nanotubes," "nanocrystals," "nanobeads," "nanobelts," "nanomaterial," and "nanodisks."

As used herein, the term "nanoscale" refers to a dimension that is no greater than 500 nm. In some embodiments, a nanoscale dimension can have a dimension that is no greater than 100 nm. The terms "nanoscale particle" and "nanoparticle" are used interchangeably in the present invention.

Reference will now be made in detail to exemplary embodiments of the disclosed technology, examples of which are illustrated in the accompanying drawings and disclosed herein. Wherever convenient, the same references numbers will be used throughout the drawings to refer to the same or like parts.

Figure 2:
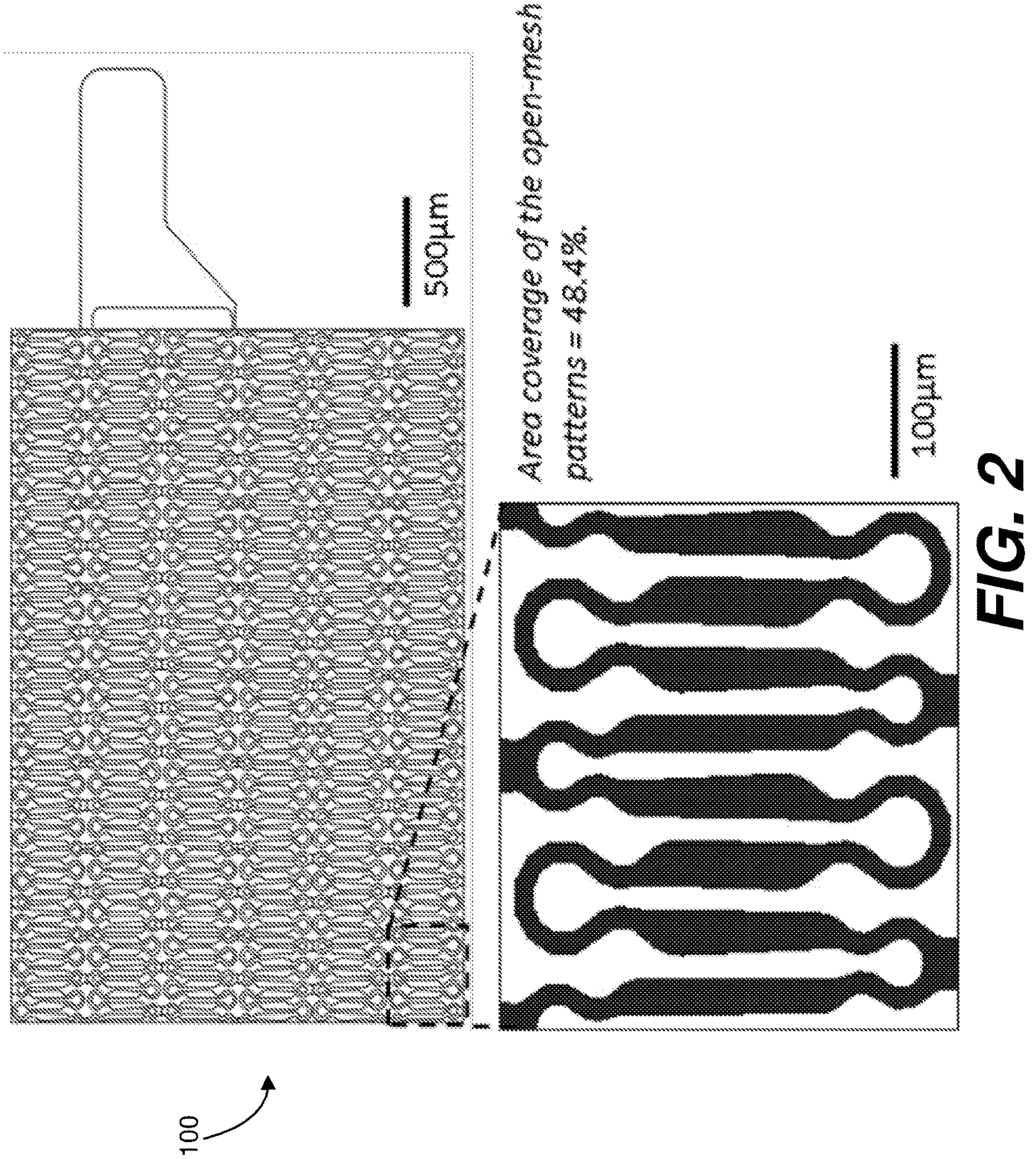
FIG. 2 illustrates a top view of an implantable cerebral sensor according to some examples of the present disclosure.

FIGS. 1 and 2 illustrate an example of an implantable cerebral sensor 100. As shown, the sensor 100 can comprise an insulator layer 110, a first electrode 120, a second electrode 140, and a dielectric layer 130 electrically separating the first electrode 120 and the second electrode 140. The various layers of the sensor 100 can be disposed on top of one another, or in any sequential order. In some examples, the sensor 100 can further comprise an outer shell (not shown) to substantially encase some and/or all of the layers of the sensor 100. For instance, the outer shell can comprise an elastomer.

The insulator layer 110 and the dielectric layer 130 can be made from substantially the same material. For example, the insulator layer 110 and the dielectric layer 130 can be made from a polymer, such as a polyimide. However, the insulator layer 110 and the dielectric layer 130 need not be made from the same material. For example, the layers can be made from different polymers. The insulator layer 110 and the dielectric layer 130 can also be selected based on other material properties desired to be conferred to the sensor 100, including, but not limited to, Young's modulus (elastic modulus), elasticity, Poisson's ratio, shear modulus, and the like.

For example, it can be desirable for the sensor 100 to be highly flexible such that the introduction of a fluid flow can easily cause deflection. Therefore, the insulator layer 110 and/or the dielectric layer 130 can have a Young's modulus from 1 MPa to 100 GPa (e.g., from 10 MPa to 100 GPa, from 50 MPa to 100 GPa, from 100 MPa to 100 GPa, from 150 MPa to 100 GPa, from 200 MPa to 100 GPa, from 250 MPa to 100 GPa, from 300 MPa to 100 GPa, from 350 MPa to 100 GPa, from 400 MPa to 100 GPa, from 450 MPa to 100 GPa, from 500 MPa to 100 GPa, from 550 MPa to 100 GPa, from 600 MPa to 100 GPa, from 650 MPa to 100 GPa, from 700 MPa to 100 GPa, from 750 MPa to 100 GPa, from 800 MPa to 100 GPa, from 850 MPa to 100 GPa, from 900 MPa to 100 GPa, from 950 MPa to 100 GPa, from 1 GPa to 100 GPa, from 1 GPa to 90 GPa, from 1 GPa to 80 GPa, from 1 GPa to 70 GPa, from 10 GPa to 100 GPa, from 20 GPa to 100 GPa, from 30 GPa to 100 GPa, from 10 GPa to 90 GPa, from 20 GPa to 80 GPa, from 30 GPa to 70 GPa, or from 40 GPa to 60 GPa).

The dielectric layer 130 can have a thickness sufficient to electrically separate the first electrode 120 and the second electrode 140. In other words, the dielectric layer 130 can prevent shorting by ensuring that the first electrode 120 and the second electrode 140 do not come into electrical communication with one another. The dielectric layer 130 can have a thickness from 1 μm to 100 μm (e.g., from 1 μm to 90 μm, from 1 μm to 80 μm, from 1 μm to 70 μm, from 1 μm to 60 μm, from 1 μm to 50 μm, from 1 μm to 40 μm, from 1 μm to 30 μm, from 1 μm to 20 μm, from 1 μm to 10 μm, or from 1 μm to 5 μm).

The first electrode 120 and the second electrode 140 can be made from substantially the same material. For example, the first electrode 120 and the second electrode 140 can comprise a conductor, such as metal nanoparticles. A conductor can be any material known to a person of ordinary skill in the art capable of maintaining a flow of electrons. For example, the first electrode 120 and the second electrode 140 can comprise a transition metal as the conductor. The transition metal can be in the form of transition metal-containing nanoparticles. It is understood that the first electrode 120 and the second electrode 140 can be made from substantially different materials as long as the materials are conductive. The conductive materials can also be selected based on other material properties desired to be conferred to the sensor 100, including, but not limited to, conductivity, resistivity, capacitance, tensile strength, tear strength, puncture resistance and the like.

In some examples, the first electrode 120 and the second electrode 140 can have a Young's modulus from 1 GPa to 100 GPa (e.g., from 1 GPa to 90 GPa, from 1 GPa to 80 GPa, from 1 GPa to 70 GPa, from 10 GPa to 100 GPa, from 20 GPa to 100 GPa, from 30 GPa to 100 GPa, from 10 GPa to 90 GPa, from 20 GPa to 80 GPa, from 30 GPa to 70 GPa, or from 40 GPa to 60 GPa).

The first electrode 120 and the second electrode 140 can have a thickness configured to confer a desirable property to the sensor 100. For example, the thickness can be selected to improve the flatness and/or uniformity of the first electrode 120 and the second electrode 140. The first electrode 120 can have a thickness from 1 μm to 100 μm (e.g., from 1 μm to 90 μm, from 1 μm to 80 μm, from 1 μm to 70 μm, from 1 μm to 60 μm, from 1 μm to 50 μm, from 1 μm to 40 μm, from 1 μm to 30 μm, from 1 μm to 20 μm, from 1 μm to 10 μm, or from 1 μm to 5 μm). The second electrode 140 can have a thickness from 1 μm to 100 μm (e.g., from 1 ttm to 90 μm, from 1 μm to 80 μm, from 1 μm to 70 μm, from 1 μm to 60 μm, from 1 μm to 50 μm, from 1 μm to 40 μm, from 1 μm to 30 μm, from 1 μm to 20 μm, from 1 μm to 10 μm, or from 1 μm to 5 μm). The first electrode 120 and the second electrode 140 can have substantially similar thicknesses; however, the thicknesses can also be substantially different.

As would be appreciated, the individual properties of the insulator layer 110, the first electrode 120, the dielectric layer 130, and the second electrode 140 can confer desirable properties to the overall sensor 100. For instance, the respective Young's moduli of the respective layers can ensure the sensor 100 has the ability to bend 90° or greater around a 1 mm diameter (e.g., 100° or greater, 110° or greater, 120° or greater, 130° or greater, 140° or greater, 150° or greater, 160° or greater, 170° or greater, or 180° or greater). In some examples, the sensor 100 has the ability to bend 360° or less around a 1 mm diameter (e.g., 350° or less, 340° or less, 330° or less, 320° or less, 310° or less, 300° or less, 290° or less, 280° or less, 270° or less, 260° or less, 250° or less, 240° or less, 230° or less, 220° or less, 210° or less, 200° or less, or 190° or less). In some examples, the sensor 100 can bend from 180° to 360° around a 1 mm diameter without resistance increasing (i.e., the electrical resistance of the sensor 100 changes positively or negatively by 1Ω or less during bending).

By way of another example, the respective thicknesses of the layers can ensure that the sensor has desirable electrical properties. For example, the sensor 100 can have a capacitance from 1 pF to 1000 pF (e.g., from 1 pF to 900 pF, from 1 pF 800 pF, from 1 pF to 700 pF, from 1 pF to 600 pf, 1 pF to 500 pF, from 1 pF to 400 pF, from 1 pF to 300 pF, from 1 pF to 200 pF, from 1 pF to 100 pF, from 10 pF to 100 pF, from 20 pF to 100 pF, from 30 pF to 100 pF, from 40 pF to 100 pF, from 50 pF to 100 pF, from 1 pF to 90 pF, from 1 pF to 80 pF, from 1 pF to 70 pF, from 1 pF to 60 pF, or from 1 pF to 50 pF).

By way of another example, the sensor 100 can stretch under a strain of from 250% to 1000% (e.g., from 250% to 950%, from 300% to 900%, from 350% to 850%, from 400% to 800%, from 450% to 750%, from 500% to 700%, from 500% to 1000%, or from 250% to 500%) without resistance increasing (i.e., the electrical resistance of the sensor 100 changes positively or negatively by 1Ω or less during bending).

Figure 3A:
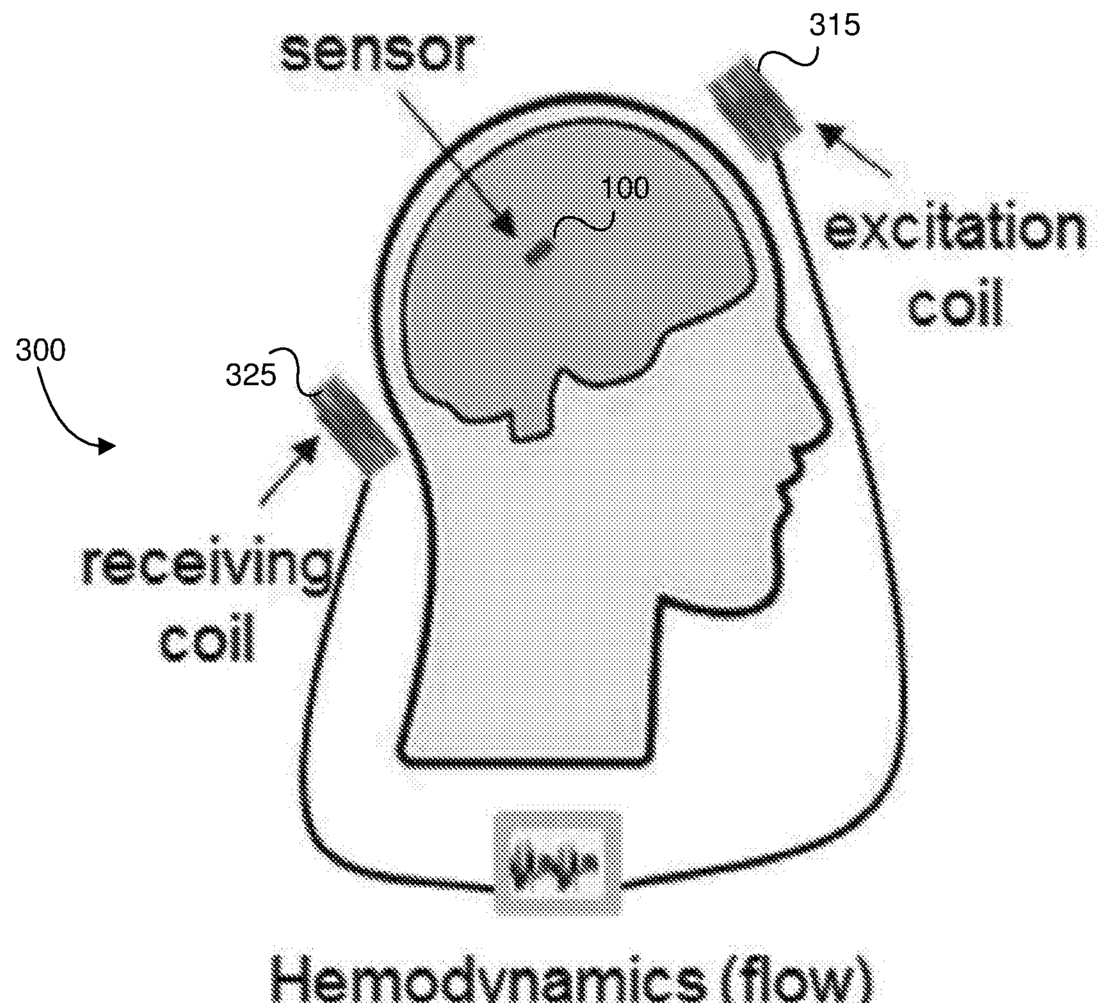
FIG. 3A illustrates a system for hemodynamic monitoring of blood vessels according to some examples of the present disclosure.
Figure 3B:
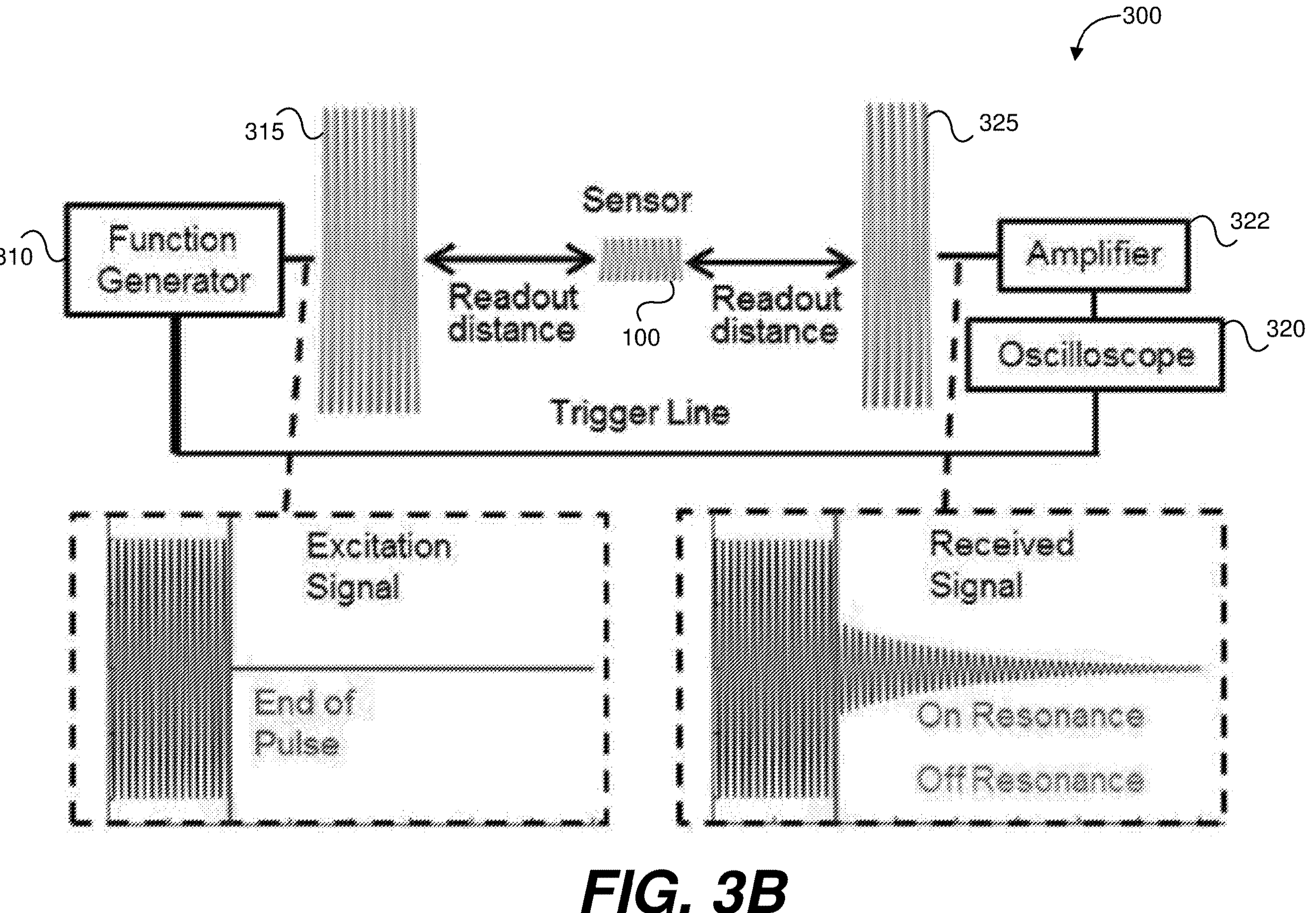
FIG. 3B is a component diagram of a system for hemodynamic monitoring of blood vessels according to some examples of the present disclosure.

FIGS. 3A and 3B illustrate an example system 300 for hemodynamic monitoring of blood vessels utilizing the implantable cerebral sensor 100. The hemodynamic properties that can be monitored by the system 300 can include, but are not limited to, flow velocity, flow rate, blood pressure, blood viscosity, plasma viscosity, osmotic pressure, red blood cell count, hemodilution, cardiac output, vessel throughput, blood turbulence, vascular resistance, wall tension, stress, strain, capacitance, and the like. As shown, the system 300 can include the sensor 100, a function generator 310, and an oscilloscope 320. The function generator 310 can be in communication with and connected to an excitation coil 315, and the oscilloscope 320 can be in communication with and connected to a receiving coil 325. The oscilloscope 320 can also be in communication with and connected to an amplifier 322 configured to receive and amplify signals received at the receiving coil 325. In such a manner, a wireless circuit can be formed between the excitation coil 315, the sensor 100, and the receiving coil 325.

Figure 4A:
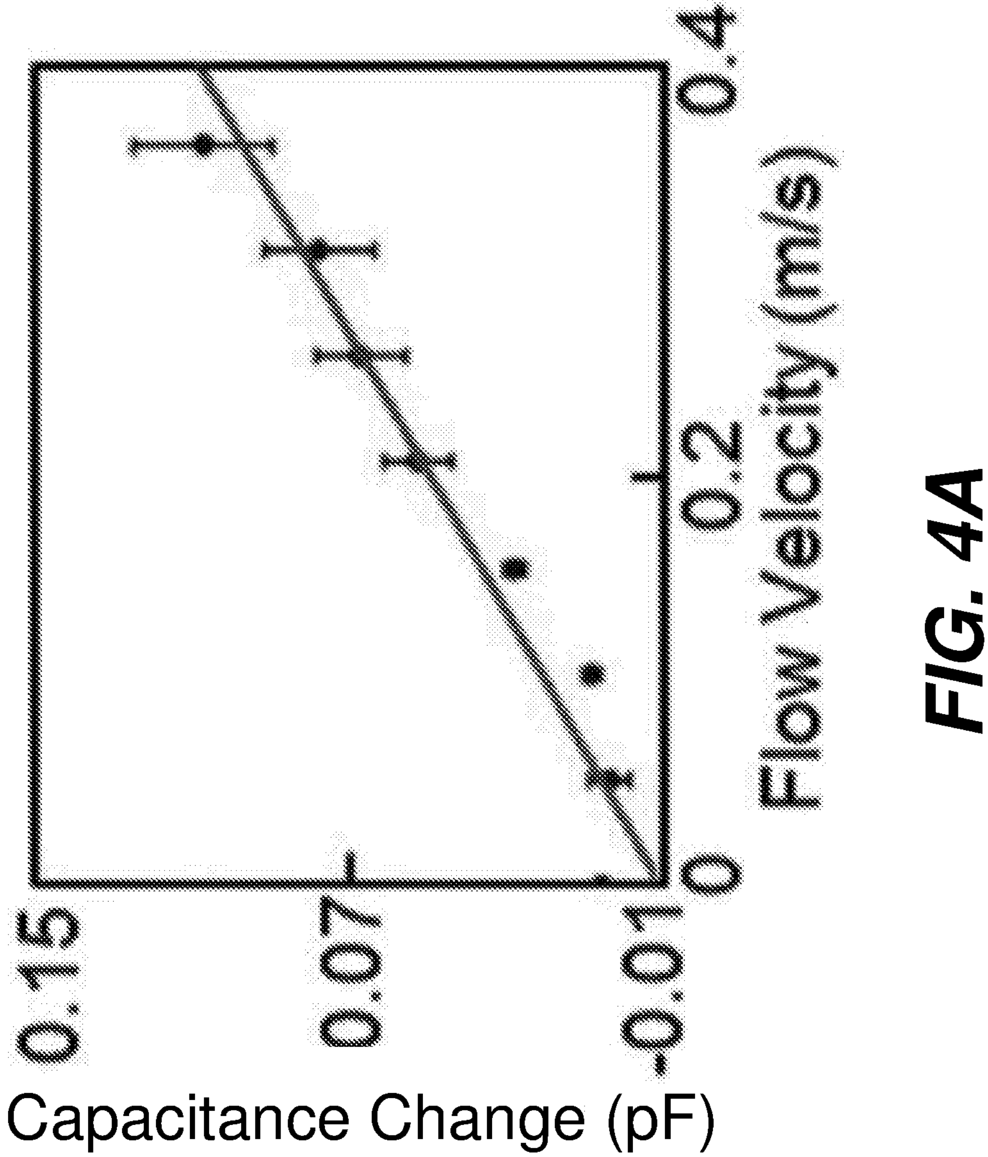
FIGS. 4A-C illustrate charts of correlations between implantable cerebral sensor properties and hemodynamic properties according to some examples of the present disclosure.
Figure 4B:
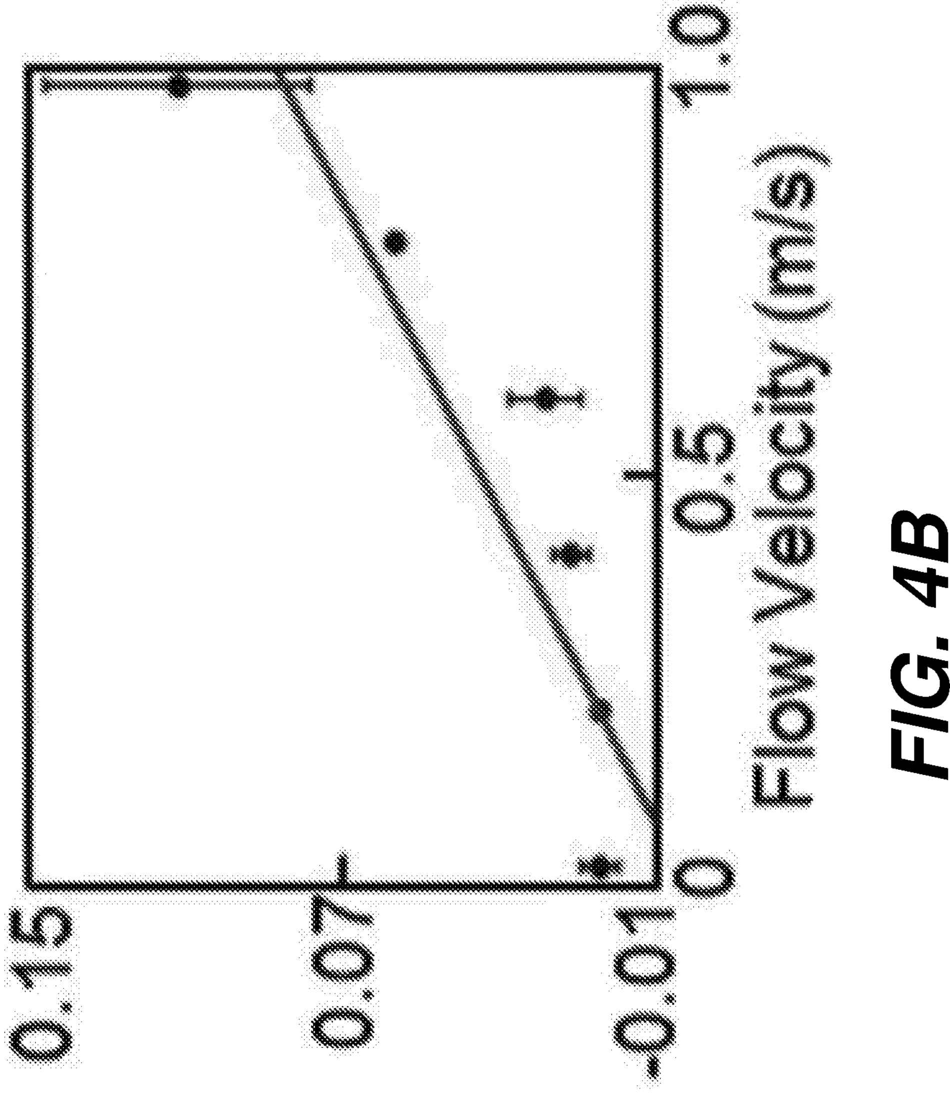
Figure 4C:
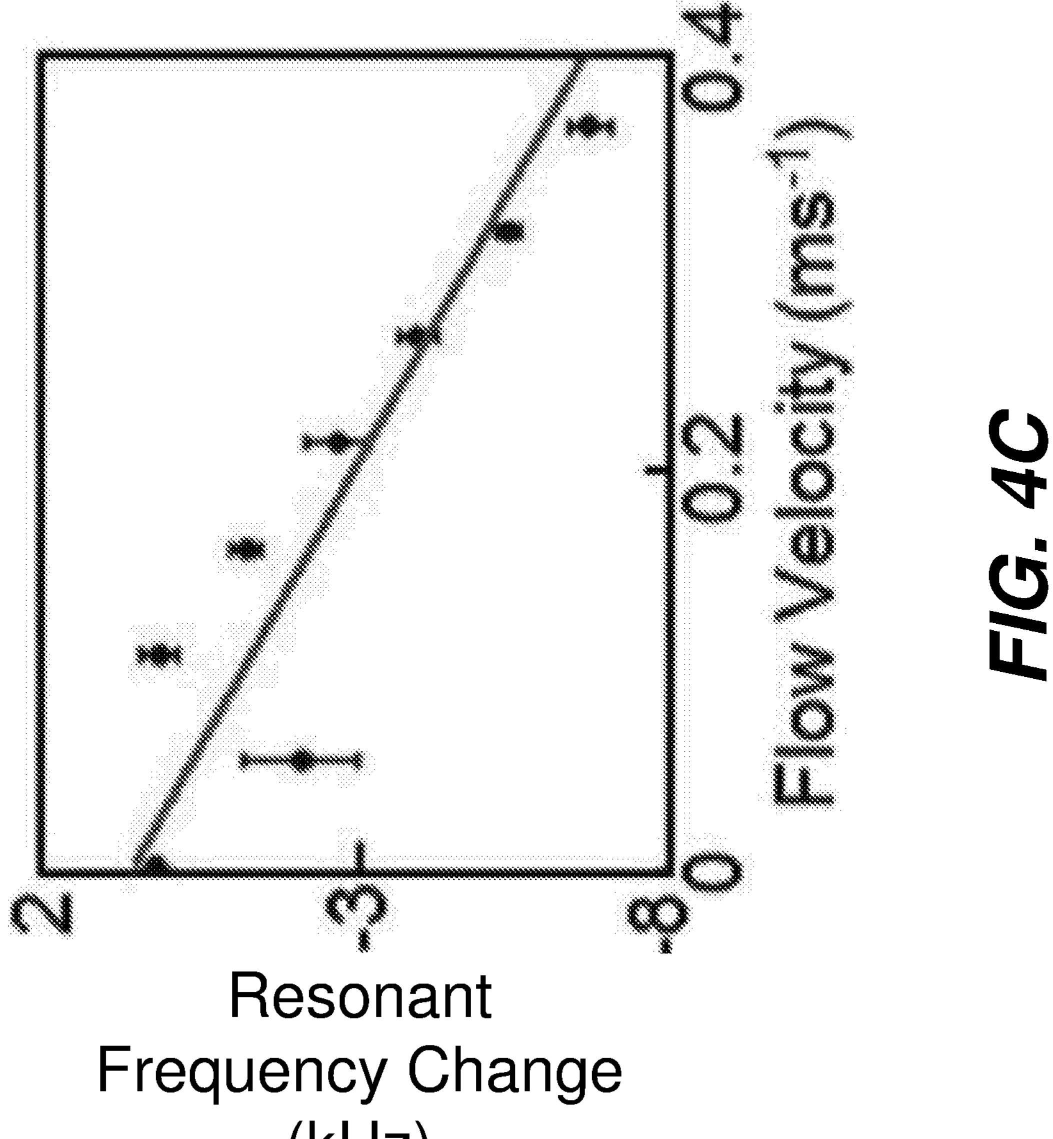

In such a manner, a first signal can be generated by the function generator 310 and transmitted by the excitation coil 315. The signal can interact with the sensor 100 and can be received by the oscilloscope 320 at the receiving coil 325. The signal received by the receiving coil 315, after interacting with the sensor 100, can be indicative of a change in the resonant frequency amplitude of the sensor 100. Therefore, the system 100 can provide for wireless transmission and communication to and from the sensor 100. The disclosed wireless readout methods can apply inductive coupling principles between the implanted cerebral sensor 100 and two (or more) external coils to record transient signals. Upon receiving a signal, the system 300 can transform and correlate the received resonant frequency response and sensor capacitance with a flow velocity through the sensor 100. Example correlations can be seen in FIGS. 4A, 4B, and 4C.

A capacitive sensor, combined with an inductive coil, forms a circuit with a resonant frequency defined as:

$$f = \frac{1}{2\pi\sqrt{LC}} \tag{1}$$

where L is inductance and C is sensor capacitance. Such a readout method, compared to the frequency domain method of observing impedance changes, has been proven to achieve longer readout distances.

Figure 5A:
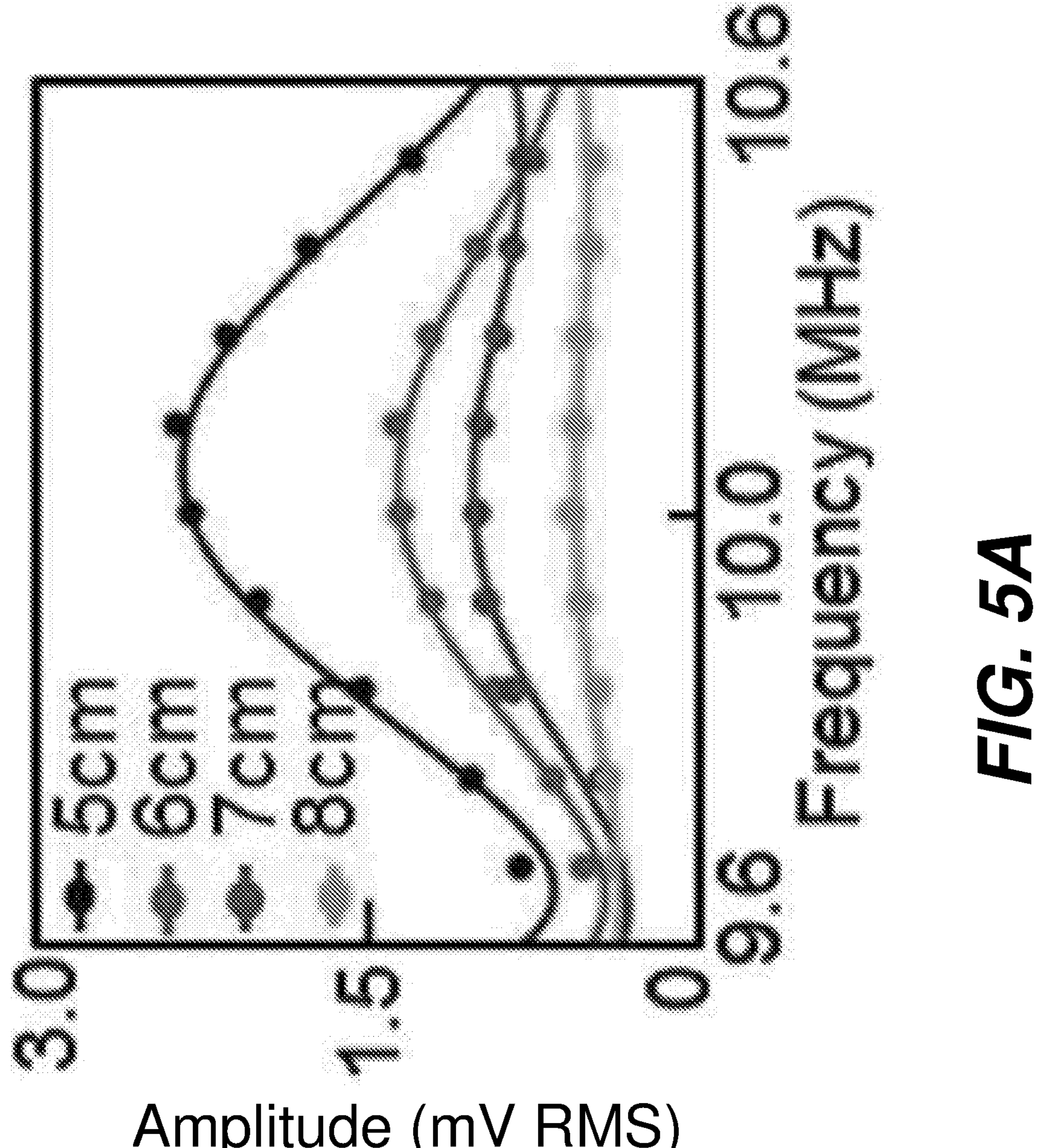
FIGS. 5A-C illustrate various readout distances for an implantable cerebral sensor in different media according to some examples of the present disclosure.
Figure 5B:
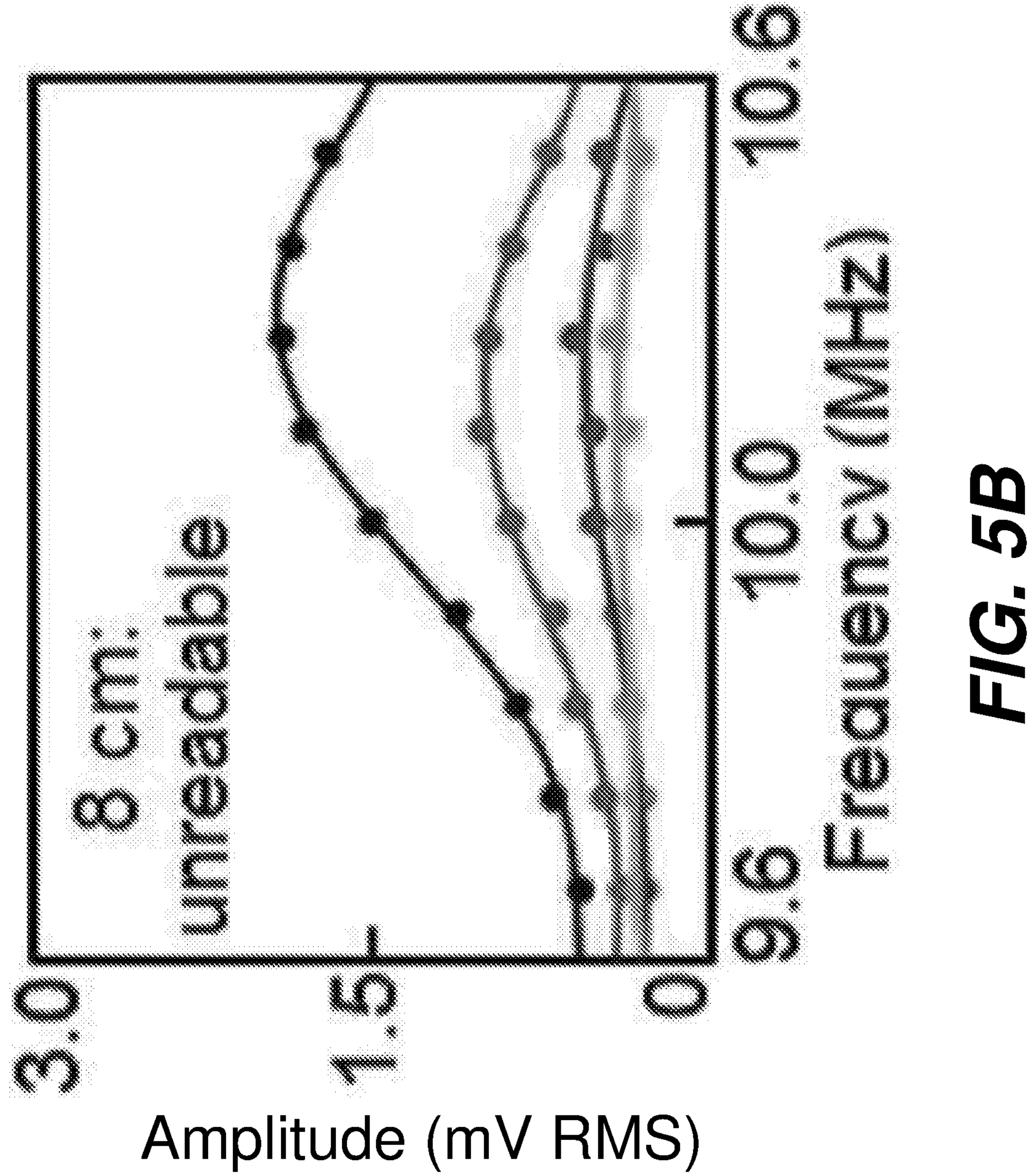
Figure 5C:
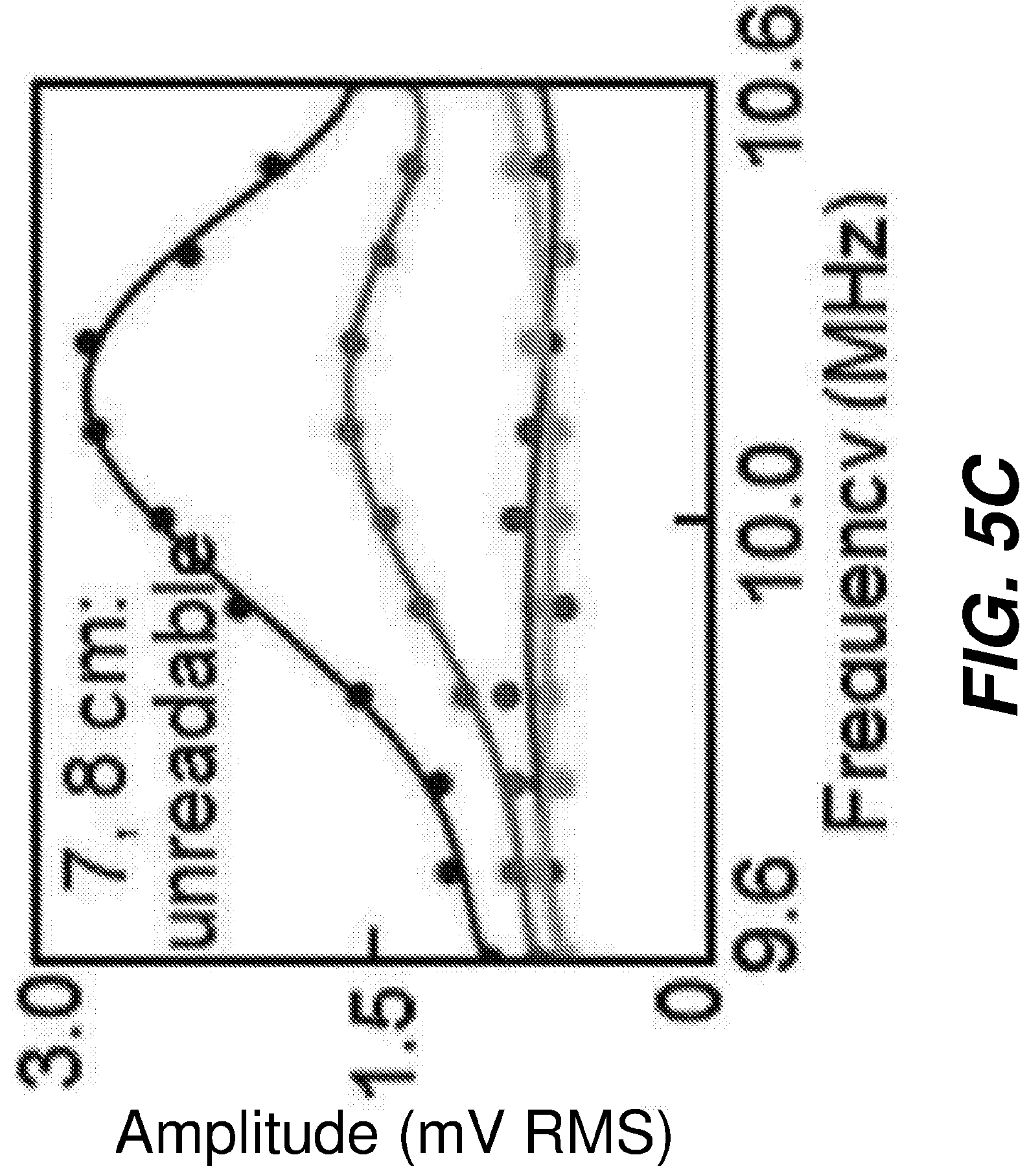

The root-mean-square (RMS) amplitudes of transient signals after excitation are compared to identify sensor resonance, as shown. During the measurement, the overall readout range can be defined as the distance between the end of the sensor 100 and the nearest external coil (either excitation coil 315 or receiving coil 325). Analytical study can play a key role in understanding the key parameters of resonant frequency, quality factor, and power transfer efficiency to optimize a sensor design. Increasing conductive cross-sectional area for a given material can improve quality factor and transfer efficiency due to a decrease in resistance. This improvement is only limited by the skin effect phenomenon. An example of the sensor 100 readout distance in air, saline solution, and in meat can be seen in FIGS. 5A, 5B, and 5C, respectively.

While the above-described methods are described with respect to the system 300, it is understood that one or more method steps or whole methods can be performed by other systems, general-purpose computers, computer operators, and the like.

Figure 6A:
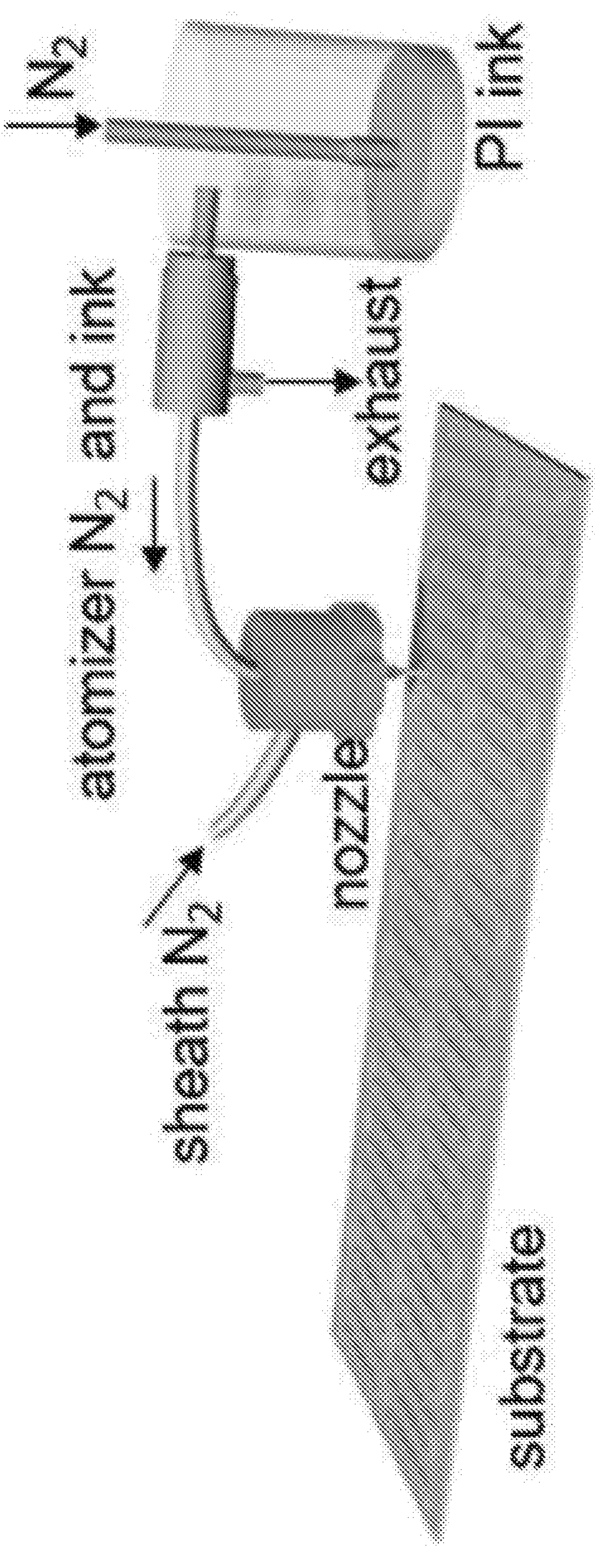
FIG. 6A illustrates a system for manufacturing implantable cerebral sensors according to some examples of the present disclosure.
Figure 6B:
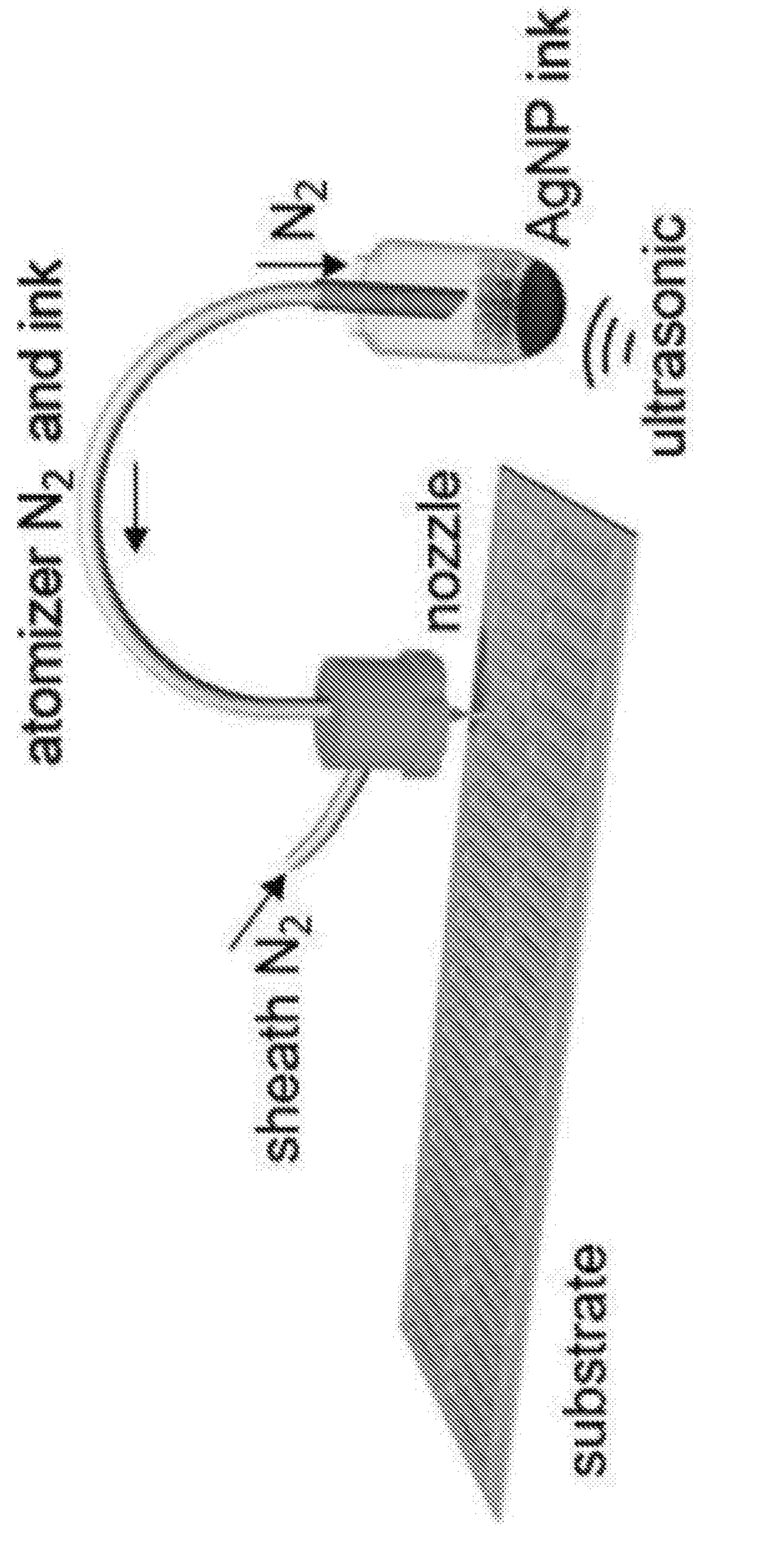
FIG. 6B illustrates another system for manufacturing implantable cerebral sensors according to some examples of the present disclosure.

Also disclosed herein are systems and methods for making the implantable cerebral sensors disclosed herein. The disclosed methods can use aerosol jet printing (AJP) techniques. FIGS. 6A and 6B illustrate systems for making the disclosed implantable cerebral sensors. As shown, an aerosol jet printer can atomize desired inks to deposit the materials on a substrate. Although the following methods are described with respect to the systems shown in FIGS. 6A and 6B, it is understood that one or more method steps or whole methods can be performed by other similar systems configured to carry out similar functions. The following methods are also described with respect to the sensor 100, but it is understood that the following methods can be used to make any desired sensor.

Figure 7:
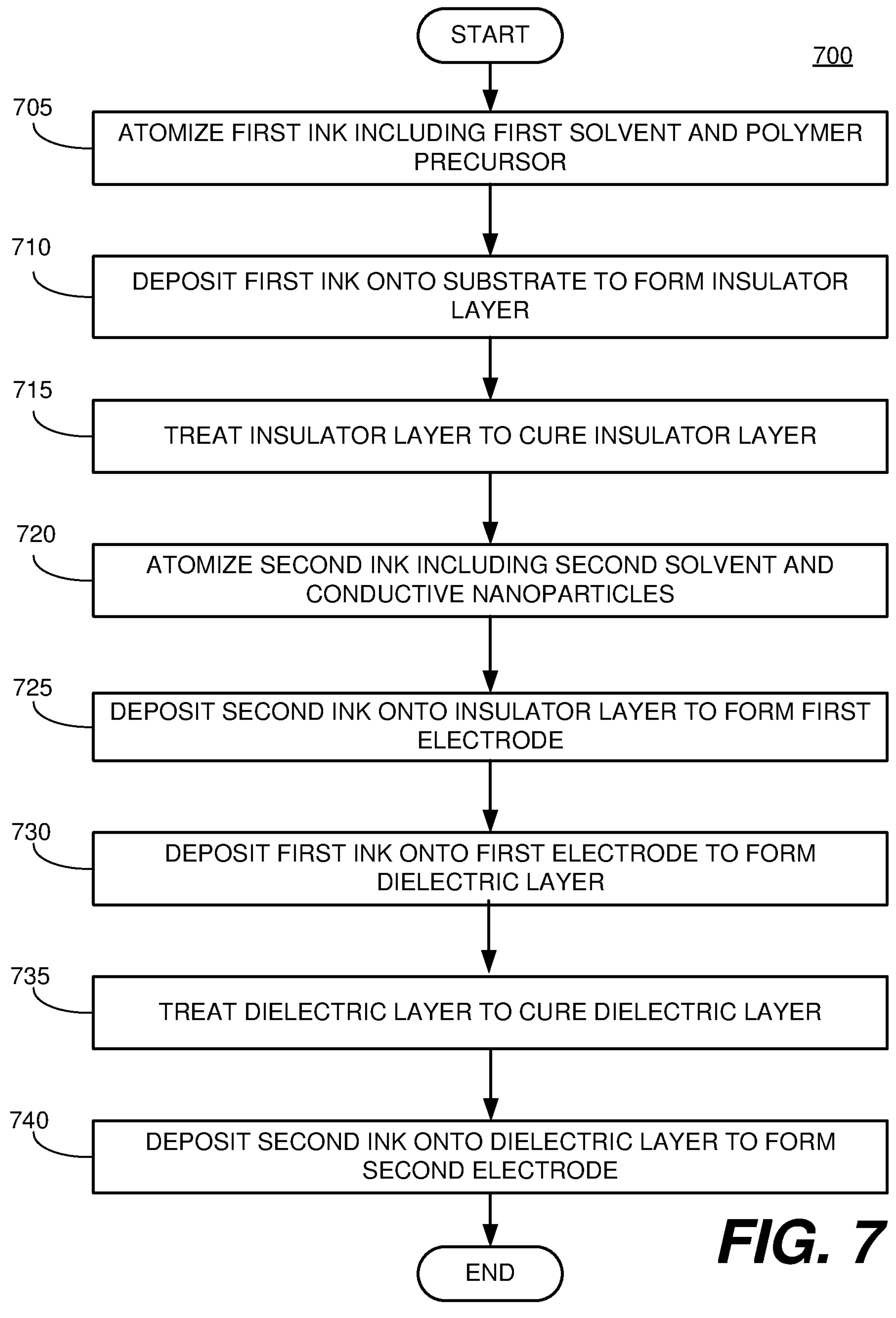
FIG. 7 illustrates a flow chart of a method for making implantable cerebral sensors according to some examples of the present disclosure.

FIG. 7 illustrates a flowchart of a method 700 of making an implantable cerebral sensor. In block 705, a first ink is atomized. The first ink can include a first solvent and a polymer precursor. The volume ratio of the components in the first ink can be optimized. The first solvent can be any solvent capable of dissolving the polymer precursor to create a substantially homogeneous solution. The method can then proceed to block 710 or to other method steps not shown.

In block 710, the first ink can be deposited onto a substrate to form the insulator layer 110. The substrate can be made of glass or any suitable substrate wherein the printed sensor can be easily detachable. Multiple passes, or deposits, of the first ink can be made to ensure a uniform covering of the first ink. Any number of passes can be made to ensure that the insulator layer 110 is formed with a sufficient thickness and smoothness. The printing speed can also be selected such that the insulator layer 110 is formed with a sufficient thickness and smoothness. The printing speed can also be optimized to balance fabrication time with surface smoothness. The method can then proceed to block 715 or to other method steps not shown.

In block 715, the first insulator 110 can be treated. The treating can include curing the first insulator layer 110 to solidify the polymer precursor in the first ink and to also improve the surface adhesion of the first insulator layer 110. For example, the treating can include a plasma treatment. The method can then proceed to block 720 or to other method steps not shown.

In block 720, a second ink can be atomized. The second ink can include conductive nanoparticles and a second solvent. The volume ratio of the components in the second ink can be optimized. The second solvent can be any solvent capable of dissolving the conductive nanoparticles to create a substantially homogeneous solution. The atomization can utilize an ultrasonic atomizer. The method can then proceed to block 725 or to other method steps not shown.

In block 725, the second ink can be deposited onto the first insulator layer 110 to form the first electrode 120. Multiple passes, or deposits, of the second ink can be made to ensure a uniform covering of the second ink. Any number of passes can be made to ensure that the first electrode 120 is formed with a sufficient thickness and smoothness. For electrical performance, a thick layer can be desirable. Careful attention can also be paid to the Gaussian profile of the first electrode 120 to ensure proper construction of the sensor 100. The first electrode 120 can also be sintered as a final treatment step. The method can then proceed to block 730 or to other method steps not shown.

In block 730, the first ink can be deposited onto the first electrode 120 to form the dielectric layer 130. The first ink can be deposited such that the first electrode 120 is substantially covered by the dielectric layer 130. Although a thin dielectric layer can provide a high sensitivity and high capacitance for a given area, a thin dielectric layer may not fully cover the first electrode 120 if the first electrode 120 has many uneven profiles. Therefore, to prevent shorting, the dielectric layer 130 can be deposited such that the profiles of the first electrode 120 are substantially covered. Multiple passes, or deposits, of the first ink can be made to ensure a uniform covering of the first ink. Any number of passes can be made to ensure that the dielectric layer 130 is formed with a sufficient thickness and smoothness. The printing speed can also be selected such that the dielectric layer is formed with a sufficient thickness and smoothness. The printing speed can also be optimized to balance fabrication time with surface smoothness. The method can then proceed to block 735 or to other method steps not shown.

In block 735, the dielectric layer 130 can be treated. The treating can include curing the dielectric layer 130 to solidify the polymer precursor in the first ink and to also improve the surface adhesion of the dielectric layer 130. For example, the treating can include a plasma treatment. The method can then proceed to block 740 or to other method steps not shown.

In block 740, the second ink can be deposited onto the dielectric layer 130 to form the second electrode 140. Multiple passes, or deposits, of the second ink can be made to ensure a uniform covering of the second ink. Any number of passes can be made to ensure that the second electrode 140 is formed with a sufficient thickness and smoothness. For electrical performance, a thick layer can be desirable. Careful attention can also be paid to the Gaussian profile of the second electrode 140 to ensure proper construction of the sensor 100. The second electrode 140 can also be sintered as a final treatment step. The method can terminate or continue on to other method steps not shown.

For example, after block 740, the sensor 100 can be encased. The encasing can include an elastomer layer to substantially surround all the printed layers of the sensor 100. The encased sensor 100 can then be integrated or placed within a stent, and the stent can be configured to be implanted within a blood vessel.

As used in this application, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Certain embodiments and implementations of the disclosed technology are described above with reference to block and flow diagrams of systems and methods according to example embodiments or implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some embodiments or implementations of the disclosed technology.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

EXAMPLES

The following exemplary use cases describe examples of a typical user flow pattern. They are intended solely for explanatory purposes and not limitation.

Example 1. The sensor fabrication can utilize conventional microfabrication techniques, combined with a transfer printing and hard-soft integration method. Spin-casting can be used to deposit poly(methyl methacrylate) (PMMA; 100 nm in thickness) and polyimide (PI; 1.4 μm in thickness) layers on a prepared glass slide or Si wafer. The serpentine patterns of the bottom capacitive layer can be created by photolithography and wet etching of sputter-deposited metals. The dielectric layer (PI) can be spin-coated onto the bottom metal layer, and the same process can be used to create the top capacitive metal layer. After a top PI layer is deposited, a final photoresist mask can be applied, and reactive ion etching can be used to remove all unwanted PI and finalize the mesh patterning for the sensor. The structure can be released from the carrying substrate by submerging in acetone to dissolve the PMMA sacrificial layer. Water-soluble tape (3M) can allow for retrieval of the completed sensor and transfer to a silicone elastomer (Ecoflex 00-30, Smooth-On).

Finite element analysis (ABAQUS, Dassault Systems) was used for the radial stretching and bending study. In the radial stretching, a deformable cylindrical surface was added as an expander and meshed with SFM3D4R elements (4-node quadrilateral surface element). The contact between the expander and sensor was modeled as frictionless in the tangential direction and hard contact in the normal direction. The applied strains to the sensor were up to 500%, which was increased incrementally over time. For the bending model, a deformable cylinder was added and aligned with the sensor coaxially and was meshed with C3D8R elements. A tie constraint was applied on the contact surface between the outer base support and inner sensor surface to ensure proper contact. A pair of rigid cylindrical surfaces were added to the top and base support, after which an upward displacement was applied to cause bending on the sensor. The contact between the rigid support faces and the base support surface was modeled as frictionless in the tangential direction and hard contact in the normal direction.

For the experimental study, mean vessel velocities were chosen as 0.032, 0.067, 0.097, 0.125, and 0.142 m/s. A testing model was designed with the same design as in the computational model; PDMS was used to make an aneurysm replica from a tube (5 mm in diameter) with an aneurysm sac (7 mm in diameter). A pulsatile pump (55-1838, Harvard Apparatus) was used to drive the flow of a blood through the model at a rate of 60 strokes per minute. The stroke volume was adjusted to match with the modeled flow rates. For data acquisition, flexible microwires were attached to the sensor before encapsulation. An LCR meter (BK Instruments) was used to record capacitive change from a sensor through the CP-D function at a rate of 7.5 kHz and 0.5 V.

Example 2. A silicon substrate can be first prepared by cleaning in an acetone and isopropanol bath, after which it can be thoroughly rinsed with deionized (DI) water and air dried with a nitrogen gun. Then the substrate can be cleaned with an oxygen plasma etch at 50 W and 20 sccm of $O_2$, for 60 seconds. Afterwards, the fabrication process can begin. The first step can be to deposit the sacrificial and bottom support layers. For the sacrificial layer, Polymethyl methacrylate (PMMA-495, MicroChem, USA) can be deposited via spin coating at 2000 rpm for 30 seconds, and baked at 180° C. for 2.5 minutes. Then a layer of Polyimide (PI; PI-2545, HD MicroSystems, USA) can be spin coated at 4000 rpm for 60 seconds, soft baked at 150° C. for 5 minutes and hard bake at 200° C. for 45 minutes. After cooling, the layers are treated with $O_2$ plasma cleaning (50 W, 20 sccm, for 30 seconds). Next, the bottom metal layer can be applied using sputter deposition (NiTi; 300 nm, Mg; 300 nm, or Cr/Au; 10 nm/100 nm). After metal deposition, Photoresist (PR; SPR 3012, MicroChem, USA) can be spin coated at 2000 rpm for 30 seconds and baked at 90° C. for 1.5 minutes. Next, the PR can be exposed to UV-light under a metal layer mask for 3.5 seconds at 365 nm. In step four, the sensor pattern can be developed with MF-CD 26, which takes about 30 seconds to fully develop. After rinsing, the metal layer can be masked with the desired sensor pattern, and now wet etching of the bottom metal layer can be performed. Each metal can use a different chemical treatment, and the following wet etchants can be used: NiTi: 1% nitric acid, 2% hydrofluoric acid, 97% DI water; Mg: 0.25% nitric acid, 0.75% acetic acid, 4% ethanol, 95% DI water; Au: Gold Etch—Type TFA (Transene Company, Inc.). Also, for bottom layer only; Cr: CEP 200 Mico-chrome etchant (Chemtrec).

After the bottom metal layer has been etched, the substrate can be rinsed with acetone to remove the PR and then DI water to clean it. Once clean, the PI dielectric layer can be spin coated with the same procedure utilized in the deposition of the bottom support layer. Next, using sputter deposition, the top metal layer can be deposited (300 nm for NiTi or Mg, or 100 nm for Au). Similar to the bottom metal layer, after deposition is complete, PR (SPR 3012) can be spin coated, exposed, and developed with the same aforementioned parameters. The substrate can be rotated 180 degrees under the metal mask to allow for a mirrored top metal layer. The process can continue on, where the top metal layer can be wet etched using the respective etchant for each metal. Afterwards, like the first metal layer, an acetone rinse can be used to remove the PR mask, followed by a cleaning. Next, the top PI layer can be spin-coated, which can follow the same parameters as the other PI layer depositions. After the sensor layer structure is complete, spin coating can be used to deposit PR (AZ 4620, MicroChem, USA) at 2000 rpm for 30 seconds, followed by a bake at 110° C. for 5 min. The PR can then be exposed to UV-light for 20 seconds at 365 nm under the sensor mask. After exposure, the PR mask can be developed and the final pattern can be created using a developer (AZ 400K) in a ratio 1:3 DI water for about 60 seconds. Subsequently, all PI layers can be dry etched using RIE (Trion Mini-Lock Phantom III ICP, Trion Technology) of $O_2$ plasma, at 20 sccm and 150 W for 10 minutes. After the exposed PI has been etched, the substrate with sensors can be submerged in acetone bath to remove PR and sacrificial PMMA, releasing the sensor from substrate (60° C. for 2+ hours).

Example 3. Sensor fabrication can use an aerosol jet printer for all sensor layers. A sacrificial layer of PMMA can be spin-coated on a glass slide at 4000 RPM for 30 s and baked at 180° C. for 2 min. PI ink can be prepared by mixing PI-2545 precursor with NMP in a 4:1 ratio. A patterned layer of PI can be deposited via aerosol jet printer in 3 passes using a 300 μm nozzle diameter. The printed PI can be cured at 240° C. for 1 h. Next, 10 passes of silver can be printed onto the PI using AgNP ink and a 200 μm nozzle diameter. The AgNP layer can then be sintered at 240° C. for 1 h. The dielectric layer of 4 passes of PI can be printed and cured using the same parameters as before. The final silver layer can be printed and sintered with identical parameters. The PMMA layer can be dissolved in an acetone bath prior to transfer to a thin layer of Ecoflex gel spin coated at 1500 RPM on a PVA film. The top and bottom of the sensor can be attached to a stent with a small amount of Ecoflex.

All finite element analysis simulations can be performed in Abaqus (Dassault Systems). The radial stretching analysis can use a deformable, hollow cylinder to expand the sensor pattern. Sensor layers included can be elastomer encapsulation, two PI layers, and two Ag layers. The cylinder can be radially displaced to achieve 250% strain. The bending model can employ a solid, deformable cylinder that was deformed by three rigid cylinders to achieve 180° bending. The bending radius can be 0.5 mm. A tie constraint between the support cylinder and inner sensor encapsulation can ensure uniform contact.

The wireless readout method can apply inductive coupling principles between a sensor coil in a flow-diverter system and two external coils to record transient signals and measure sensor resonance. An excitation external coil (8 AWG copper wire), connected to a function generator (Keysight), can transmit a pulse of 20 sine cycles at a specified frequency and maximum amplitude (10 peak-to-peak voltage). The readout coil, attached to a low-noise amplifier (Model ZFL-1000LN+, Mini-Circuits) and oscilloscope (Tektronix), can record the signals from the excitation coil and sensor circuit. The oscilloscope can be triggered to record the transient signal by syncing it with the function generator. The function generator and oscilloscope can be controlled by a custom Matlab program to record frequency sweep results. A maximum transient response from the sensor coil can occur when the excitation frequency matched the sensor's resonance frequency. The frequency sweep can be used between 0.001 and 0.1 MHz steps to identify resonance. Transient signals can be processed by the program to remove signal drift, identifying an appropriate RMS window that is 6 cycles in length, and calculating an RMS value for that frequency. The RMS values can be saved, and a quadratic curve can be fit to the frequency sweep. The maximum amplitude on the fitted curve can be located, and the corresponding frequency can be identified as its resonant frequency. During the measurement, three coils can be axially aligned, and the overall readout range can be defined as the distance between the end of the sensor coil and the nearest external coil.

An analytical study can optimize the system parameters, including coil length (l), coil diameter (d), and number of turns (N), which was used to improve the wireless readout distance via inductive coupling. Both internal (i) and external (e) coils can be studied. Sensor inductance (L) can be calculated with correction coefficients (Equation (2)), which can offer a more accurate estimate. The coefficient km is a mutual inductance correction for a round wire and $k_s$, is a self-inductance correction. Inductance along with sensor capacitance (C) can define sensor resonance (f). Low resonance frequency can be preferred to allow a higher magnetic field, while reducing tissue absorption from a sensor during wireless telecommunication, which can enable a long readout distance. Specific absorption rate can be a measure of safety when radio frequency was applied and known to scale with frequency by f. The readout distance of the inductive coupling method can depend on the sensor's quality factor (Q), function of inductance, capacitance, and resistance (R) (Equation (3)). The quality factor can determine the speed of response decay, efficiency of power transfer at resonance, and bandwidth. A larger quality factor can result in a more detectable transient response. Mutual inductance (M) (Equation (4)) and coupling coefficient (k) (Equation (5)) can also play roles in power transfer, and they depended on the separation distance (z). More efficient power transfer between the sensor and receiver coils can improve the readout distance. Finally, to quantify the impacts of quality and coupling on power transfer, overall transfer coefficient, (P) (Equation (6)) and transfer efficiency (h) (Equation (7)) can be defined. The maximum readout distance can be determined by varying those parameters.

$$L = \frac{\mu N^2 \pi d^2}{4l} - \mu \frac{d}{2} N(k_s + k_m), \text{ where } \mu = \text{permeability} \quad (2)$$

$$Q = \frac{1}{R}\sqrt{\frac{L}{C}} \quad (3)$$

$$M = \frac{\mu \pi N_i N_e d_i^2 d_e^2}{16\sqrt{d_i^2 + z^2}} \quad (4)$$

$$k = \frac{M}{\sqrt{L_i L_e}} \quad (5)$$

$$\Pi = \frac{k\sqrt{Q_i Q_E}}{1 + k^2 Q_i Q_e} \quad (6)$$

$$\eta = \frac{k^2 Q_i Q_e}{1 + k^2 Q_i Q_e} \quad (7)$$

3D finite element analysis (COMSOL) can calculate the induced current between the sensor coil and excitation external in air. The computational model can use 100 μm diameter copper wire and 8 AWG copper wire for the sensor and excitation coil, respectively. Induced current in the sensor coil can be calculated while varying antenna turns. For comparison with safety limits, a second finite element model of the excitation coil can simulate magnetic field strength while varying input voltage for comparison with safety limits. Additionally, to compare with a commercial implantable sensor, ERP can be calculated using electric field strength (E) and distance from the source (z) using Equation (8):

$$ERP = \frac{(Ez)^2}{30 \times 1.64} \quad (8)$$

A PDMS mold of an aneurysm and blood vessel can be created to simulate flow. The sensor can be placed over the aneurysm neck, and the mold can be sealed with additional PDMS. A pulsatile pump can generate flow through the model at 60 strokes per minute. Flow volume can be adjusted to achieve the desired flow rate. For wired measurements of capacitance, an LCR meter that measures inductance (L), capacitance (C), and resistance (R) (B&K Precision) can be connected to the sensor. For wireless monitoring, a copper coil can be connected to the capacitive sensor. Two external coils can be aligned with the sensor coil and resonant frequency was monitored.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. An implantable cerebral sensor configured to deflect in response to hemodynamics and to generate a wireless signal indicative of the hemodynamics comprising:
- an insulator layer;
- a first electrode disposed on the insulator layer;
- a dielectric layer disposed on the first electrode;
- a second electrode disposed on the dielectric layer; and
- an outer shell substantially encasing the insulator layer, the first electrode, the dielectric layer, and the second electrode;

wherein:
- the insulator layer, the first electrode, the dielectric layer, and the second electrode comprise the same length;
- the implantable cerebral sensor:
  - is a passive sensor;
  - has an unstretched length;
  - is deformably elastic when being stretched from 250% to 1000% of the unstretched length; and
  - has an electrical resistance that changes by less than or equal to 1Ω when being stretched from 250% to 1000% of the unstretched length;
- the second electrode is electrically separated from the first electrode by the dielectric layer;
- the first electrode and the second electrode each comprise a conductor;
- the insulator layer and the dielectric layer each comprise a polymer; and
- the implantable cerebral sensor is configured to:
  - deflect in response to intra-aneurysmal hemodynamics;
  - sense, based on the deflection at a neck of an aneurysm, a condition in a blood vessel; and
  - generate a wireless signal indicative of the sensed condition.

2. The implantable cerebral sensor of claim 1, wherein the first electrode and the second electrode each have a thickness from 1 μm to 10 μm.

3. The implantable cerebral sensor of claim 1, wherein the dielectric layer has a thickness from 1 μm to 10 μm.

4. The implantable cerebral sensor of claim 1, wherein the implantable cerebral sensor is conformally integrated with a stent configured to be implanted within a blood vessel.

5. The implantable cerebral sensor of claim 1, wherein the conductor comprises metal nanoparticles.

6. The implantable cerebral sensor of claim 1, wherein the outer shell comprises an elastomer.

7. The implantable cerebral sensor of claim 1, wherein the first electrode and the second electrode each have a Young's modulus from 1 GPa to 100 GPa.

8. The implantable cerebral sensor of claim 1, wherein the implantable cerebral sensor has a capacitance from 50 pF to 100 pF between the first electrode and the second electrode.

9. A method of making the passive implantable cerebral sensor of claim 1 comprising:

atomizing a first ink comprising a polymer precursor and a first solvent;

depositing the first ink onto a glass substrate to form the insulator layer;

treating the insulator layer to cure the insulator layer and to improve the surface adhesion of the insulator layer;

atomizing a second ink comprising conductive nanoparticles and a second solvent;

depositing the second ink onto the insulator layer to form the first electrode;

depositing the first ink onto the first electrode to form the dielectric layer such that the first electrode is substantially encased by the dielectric layer;

treating the dielectric layer to cure the dielectric layer and to improve the surface adhesion of the dielectric layer;

depositing the second ink onto the dielectric layer to form the second electrode; and substantially encasing the implantable cerebral sensor in an elastomer layer forming the outer shell.

10. The method of claim 9, wherein each of the depositing the second ink further comprises sintering the first electrode and the second electrode.

11. The method of claim 9, wherein the depositing the first ink forms the dielectric layer to have a thickness from 1 μm to 10 μm; and wherein the depositing the second ink forms the first electrode and the second electrode to have a thickness from 1 μm to 10 μm.

12. The method of claim 11, wherein the insulator layer and the dielectric layer have a Young's modulus from 1 MPa to 100 GPa; and wherein the first electrode and the second electrode have a Young's modulus from 1 GPa to 100 GPa.

13. The method of claim 12, wherein the implantable cerebral sensor is deformably elastic when stretched from 250% to 1000% of the original length of the implantable cerebral sensor; and wherein the implantable cerebral sensor has a capacitance from 50 pF to 100 pF between the first electrode and the second electrode.

14. The method of claim 9, wherein the ratio of the polymer precursor to the first solvent in the first ink is 4:1 by volume.

15. A system for hemodynamic monitoring of blood vessels comprising:

the implantable cerebral sensor of claim 1;

a function generator in electrical communication with an excitation coil; and an oscilloscope configured to receive a signal from an amplifier in electrical communication with a receiving coil;

wherein a circuit is formed between the excitation coil, the implantable cerebral sensor, and the receiving coil.

16. The system of claim 15, wherein the system is configured to:

wirelessly transmit a first signal from the excitation coil to the implantable cerebral sensor;

wirelessly receive a second signal at the receiving coil, the second signal being indicative of a change in the resonant frequency amplitude of the implantable cerebral sensor; and calculate a flow velocity of blood flowing through the implantable cerebral sensor based on the resonance frequency.

17. The implantable cerebral sensor of claim 1, wherein the electrical resistance change is positive or negative.

18. An implantable cerebral sensor comprising:

a first insulator layer comprising a first polymer;

a first electrode disposed on the first insulator layer and comprising a first conductor;

a dielectric layer disposed on the first electrode and comprising a second polymer;

a second electrode disposed on the dielectric layer and comprising a second conductor; and an outer shell substantially encasing the first insulator layer, the first electrode, the dielectric layer, and the second electrode;

wherein:

the second electrode is electrically separated from the first electrode by the dielectric layer;

the first electrode and the second electrode each:

have a thickness from 1 μm to 10 μm; and have a Young's modulus from 1 GPa to 100 GPa;

the dielectric layer has a thickness from 1 μm to 10 μm;

the first polymer and the second polymer each comprise a polyimide;

the first conductor and the second conductor each comprise metal nanoparticles;

the outer shell comprises an elastomer;

the implantable cerebral sensor:

is a passive sensor;

has an original length;

is deformably elastic when being stretched from 250% to 1000% of the original length; and has an electrical resistance that changes by less than or equal to 1Ω when being stretched from 250% to 1000% of the original length;

the implantable cerebral sensor has a capacitance from 50 pF to 100 pF between the first electrode and the second electrode;

the implantable cerebral sensor is conformally integrated with a stent configured to be implanted within a blood vessel; and the implantable cerebral sensor is configured to:

deflect in response to intra-aneurysmal hemodynamics;

sense, based on the deflection at a neck of an aneurysm, a condition in a blood vessel; and generate a wireless signal indicative of the sensed condition.

19. The implantable cerebral sensor of claim 18, wherein the electrical resistance change is positive or negative.

20. An implantable cerebral sensor system comprising:

a stent configured to be implanted within a blood vessel; and an implantable cerebral sensor conformally integrated with the stent, the implantable cerebral sensor comprising:

an insulator layer comprising a polyimide;

a first electrode disposed on the insulator layer and comprising metal nanoparticles;

a dielectric layer disposed on the first electrode and comprising a polyimide;

a second electrode disposed on the dielectric layer and comprising metal nanoparticles, wherein the second electrode is electrically separated from the first electrode by the dielectric layer; and an outer shell substantially encasing the insulator layer, the first electrode, the dielectric layer, and the second electrode, wherein the outer shell comprises an elastomer;

wherein:

the implantable cerebral sensor is a passive sensor;

the first electrode and the second electrode each have a thickness from 1 μm to 10 μm;

the dielectric layer has a thickness from 1 μm to 10 μm;

the implantable cerebral sensor has an unstretched length, is deformably elastic when being stretched from 250% to 1000% of the unstretched length, and has an electrical resistance that changes by less than or equal to 1Ω when being stretched from 250% to 1000% of the unstretched length;

the implantable cerebral sensor has a capacitance from 50 pF to 100 pF between the first electrode and the second electrode; and the implantable cerebral sensor is configured to:

deflect based on a fluid flow in a blood vessel;

sense, based on the deflection, a condition in the blood vessel; and generate a wireless signal indicative of the sensed condition.

* * * * *